United States Patent
Panou

(10) Patent No.: US 12,343,416 B2
(45) Date of Patent: Jul. 1, 2025

(54) SKIN ENGAGING MEMBER FOR RAZOR CARTRIDGE COMPRISING SKIN ACTIVE INGREDIENT

(71) Applicant: BIC-VIOLEX S.A., Anixi (GR)

(72) Inventor: Athanasia Panou, Agiou Athanasiou (GR)

(73) Assignee: BIC-VIOLEX S.A., Anixi (GR)

( * ) Notice: Subject to any disclaimer, the term of this patent is extended or adjusted under 35 U.S.C. 154(b) by 888 days.

(21) Appl. No.: 17/432,333

(22) PCT Filed: Feb. 28, 2020

(86) PCT No.: PCT/EP2020/055334
§ 371 (c)(1),
(2) Date: Aug. 19, 2021

(87) PCT Pub. No.: WO2020/174093
PCT Pub. Date: Sep. 3, 2020

(65) Prior Publication Data
US 2022/0151891 A1     May 19, 2022

(30) Foreign Application Priority Data
Feb. 28, 2019   (EP) ..................................... 19305238

(51) Int. Cl.
*A61K 8/36* (2006.01)
*A61Q 9/02* (2006.01)

(52) U.S. Cl.
CPC . *A61K 8/36* (2013.01); *A61Q 9/02* (2013.01)

(58) Field of Classification Search
CPC ..................................... A61K 8/36; A61Q 9/02
See application file for complete search history.

(56) References Cited

U.S. PATENT DOCUMENTS

| | | | |
|---|---|---|---|
| 5,692,302 A | 12/1997 | Booth et al. | |
| 6,589,516 B1 | 7/2003 | Eyre et al. | |
| 9,675,531 B2 * | 6/2017 | Gonzales | A61K 8/8117 |
| 2004/0132667 A1 | 7/2004 | Lintner | |
| 2012/0216408 A1 * | 8/2012 | Cook | A61Q 9/02 30/41 |
| 2013/0042482 A1 | 2/2013 | Bradford et al. | |
| 2014/0090254 A1 | 4/2014 | Bakes et al. | |
| 2014/0090255 A1 | 4/2014 | Bakes et al. | |
| 2014/0230839 A1 | 8/2014 | Coffindaffer et al. | |
| 2015/0273711 A1 | 10/2015 | Bradford et al. | |
| 2016/0008297 A1 | 1/2016 | Haustedt et al. | |

FOREIGN PATENT DOCUMENTS

| | | | |
|---|---|---|---|
| EP | 2900332 | 8/2015 | |
| EP | 2900333 | 8/2015 | |
| WO | 96/13360 | 5/1996 | |
| WO | 00/57893 | 10/2000 | |
| WO | 2008/150155 | 12/2008 | |
| WO | 2012/009298 | 1/2012 | |
| WO | WO-2012009298 A2 * | 1/2012 | ............... A61K 8/42 |
| WO | 2014/052389 | 4/2014 | |
| WO | 2014/052390 | 4/2014 | |
| WO | 2016/016582 | 2/2016 | |
| WO | WO-2016016582 A1 * | 2/2016 | ........... C07C 229/16 |

OTHER PUBLICATIONS

WO-2016016582-A1 translation from French, provided by applicant (Year: 2021).*
International Search Report dated Apr. 6, 2020 in corresponding International PCT Patent Application No. PCT/EP2020/055334, 5 pgs.
Written Opinion dated Apr. 6, 2020 in corresponding International PCT Patent Application No. PCT/EP2020/055334, 8 pgs.

* cited by examiner

*Primary Examiner* — Michael P Cohen
(74) *Attorney, Agent, or Firm* — Ruggiero McAllister & McMahon LLC

(57) ABSTRACT

A skin engaging member is attached to a razor cartridge. The skin engaging member includes a water-insoluble material and a water-soluble material. The skin engaging member also includes a thermally tolerant skin active ingredient capable of treating and/or preventing skin redness or skin irritation. The skin active ingredient can be at least one terpenic acid derivative or its salts, strombine or a salt of strombine combined with a clay, and mixtures thereof.

14 Claims, No Drawings

SKIN ENGAGING MEMBER FOR RAZOR CARTRIDGE COMPRISING SKIN ACTIVE INGREDIENT

CROSS REFERENCE TO RELATED APPLICATION

This application is a National Stage Application of International Application No. PCT/EP2020/055334, filed on Feb. 28, 2020, now published as WO2020174093 and which claims priority from EP19305238.8, filed on Feb. 28, 2019, the entire contents of each of which is incorporated herein by reference.

BACKGROUND OF THE DISCLOSURE

1. Field of the Disclosure

The present disclosure deals with a skin engaging member attached to a razor cartridge, wherein the skin engaging member comprises a water-insoluble material, a water-soluble material, and a thermally tolerant skin active ingredient suitable for treating and/or preventing skin redness or skin irritation.

2. Description of the Related Art

Due to the nature of the shaving process, the most common skin issues faced are irritations and redness of the skin. For people with sensitive skin there are some addition unpleasant feelings faced such as stinging, burning, tightness and redness. In order to avoid these issues, the use of shaving aids on razor cartridge to provide lubrication benefits and/or to deliver cosmetic or skin active ingredients during shaving is known. Such shaving aids typically comprise a water-insoluble material that provides structural integrity and a water-soluble material that provides the lubrication or delivers the active ingredient during the shave once the water-soluble material forms a solution, that may contain the skin active ingredient, upon contact with water.

The addition of various skin active ingredients into shaving aids has also been attempted. Such ingredients may thus be vitamins, botanical extracts, salts, humectants, fragrances, essential oils, silicon oils, organic oils, waxes, antioxidants, exfoliants, depilatory agents, surfactants, hair and skin conditioning agents, anti-bacterial agents, anti-microbial, anti-irritants, antiseptics, biocides, preservatives, skin cooling and soothing agents, moisturizing and hydrating agents, skin protectants. The skin active ingredients can be included in the shaving aid to be delivered onto the skin during a wet shaving process. For example, U.S. Pat. No. 5,692,302 discloses a wound healing composition delivery system in a razor, wherein the wound healing composition may further contain dipeptide-based sweeteners that can be substances including alanine in their structures.

It is also common the skin active ingredients to be included in personal care compositions that are used as auxiliaries prior to, concurrently with and/or after shaving. For example, US20140230839 discloses a personal care composition for reducing or controlling skin irritation during a hair removal process, where the composition comprises a multi-active system consisting of an extract of camellia sinesis, panthenol, and glycyrrhizinate salt. In this latter case, the composition is applied onto the skin prior to shaving and the composition is in the form of a cream, lotion, gel, foam, milk for example which are all manufactured under mild temperature and/or shear conditions. Similarly, US2004132667 discloses cosmetic compositions that can be incorporated in shaving, pre-shaving and after shaving products comprising peptides (tetrapeptides, tripeptides) combined with farnesol, phytantriol, desquamation actives, enzymes and other active ingredients, such as anti-inflammatory agents wherein the products comprise creams, lotions, ointments, gels, emulsions, dispersions, solutions, suspensions, cleansers, foundations, anhydrous preparations, shower and bath gels and washes, shampoos and scalp treatment lotions for example which all are manufactured and/or processed under mild temperature and/or shear conditions. In other embodiments, U.S. Pat. No. 6,589,516 discloses a composition in the form of an oil-in-water emulsion cream with soothing effect for use after shaving, where the composition comprises extracts of *Boswellia* plants or boswellic acid within a carrier made of fatty alcohols or fatty acids. Similarly, US2016008297 discloses a composition for cosmetic and dermatological applications, suitable for use in after shaving products for reducing or alleviating itchy skin condition(s) and skin irritation, where the composition comprises anti-inflammatory substances, anti-itch compounds and compounds that provide antagonistic effect, i.e. antagonists, particularly combined within a pharmaceutically acceptable carrier such as polyethylene glycol ester or polyethylene glycol ether.

In all prior art products, the anti-irritation, anti-redness ingredients are incorporated in cosmetic formulations used before or after shaving and are formulations in the form of creams, lotions, ointments, gels, emulsions, dispersions, solutions, suspensions and the like. All these formulations are manufactured under mild temperature and/or soft shear conditions that do not alter, or even protect, the active ingredients contained.

It has been reported, however, that in the case of the manufacturing of shaving aid such as skin engaging members that are usually manufactured by extrusion, injection-molding, laminating or compression-molding, a substantial amount of the skin active ingredients may be lost or destroyed during such manufacturing processes.

Indeed, during the production of shaving aids, such as skin engaging member, extreme temperature and/or shear conditions are present, having the consequence that contained active ingredients hardly survive the high temperature and/or high shear during such processing conditions.

The processing temperatures to make a shaving aid, such as a skin engaging member, via extrusion or injection are typically in the range from about 150 to about 300° C., while the pressure conditions are typically in the range between 250 to 2000 bar. Many of the known skin active ingredients cannot survive such processing temperatures and high shear forces during the extrusion process. Some of the skin active ingredients may partially survive the process, but fail to be delivered in desired amount and/or be effective and/or keep their activity during wet shaving. Other skin active ingredients, however, may be more resilient to temperature and processing conditions but may be too expensive and not relevant for being applied in razor industry.

As such, despite the numerous attempts to incorporate skin active ingredients into shaving aids, there is still a need for new shaving aid formulations, such as skin engaging members attached to a razor, which are less susceptible to damage the skin active ingredients during the making process yet are still suitable for use in/delivery a topological skin care treatment during shaving.

There is thus a need for razor cartridge comprising a portion to be contacted with the skin, such as a shaving aid strip, a skin engaging member or the like, that comprises a new composition comprising a skin active ingredient which would provide a more comfortable shave to the user, treat or prevent irritation, treat or prevent skin redness and contribute to skin soothing.

There is thus also a need for the skin active ingredient to be capable of withstanding the extreme temperature and/or high shear conditions which occur in the production of the shaving aid, and to remain active and be detected both qualitatively and quantitatively in the intermediate and the final product and provides cosmetic and dermatologic benefits to the skin upon and after shaving, particularly wet shaving.

DESCRIPTION

The disclosure relates to a skin engaging member attached to a razor cartridge, the skin engaging member comprising a water-insoluble material and a water-soluble material, wherein the skin engaging member comprises a thermally tolerant skin active ingredient capable of treating and/or preventing skin redness or skin irritation and being selected from the group consisting of:
- at least one terpenic acid derivative or its salts,
- strombine or salt of strombine, combined with a clay,
- and mixtures thereof.

In embodiments, the skin active ingredient treats skin irritation; prevents skin irritation; treats skin redness; and/or prevents skin redness. In embodiments, the skin active ingredient prevents and treats a symptom selected in the group comprising skin redness, skin irritation and combination thereof.

In embodiments, the salt of strombine may be selected from the group comprising sodium, disodium, ammonium, lithium, magnesium, calcium, manganese, silver, and alkali metal salts, specifically silver.

In embodiments, the clay may be selected from the group comprising kaolinite, montmorillonite, smectite, illite, chlorite, bentonite and any other suitable carrier/inert vector, e.g. bentonite, or mixtures thereof.

In embodiments, the at least one terpenic acid derivative or its salts may be a triterpenic compound, specifically pentacyclic triterpenoid compound.

In embodiments, the at least one terpenic acid derivative or its salt may be selected from the group consisting of boswellic acid, such as alpha-boswellic acid, beta-boswellic acid, 3-O-Acetyl-β-boswellic acid, 11-Keto-β-boswellic acid, 3-O-Acetyl-11-Keto-β-boswellic acid, Acetyl-11-keto-β-boswellic acid, Acetyl-α-boswellic acid, 9,11-Dehydro-α-boswellic acid, 9,11-Dehydro-β-boswellic acid, Acetyl-9,11-dehydro-α-boswellic acid, Acetyl-9,11-dehydro-β-boswellic acid, glycyrrhetinic acid/glycyrrhizic acid and its salts, such as Ammonium Glycyrrhizate/Glycyrrhizinate, Diammonium Glycyrrhizate/Glycyrrhizinate, Potassium Glycyrrhizate/Glycyrrhizinate, Dipotassium Glycyrrhizate/Glycyrrhizinate, specifically Dipotassium Glycyrrhizate/Glycyrrhizinate and mixtures thereof.

In embodiments, the at least one terpenic acid derivative or its salts may be selected in the group consisting of boswellic acid, Dipotassium Glycyrrhizate/Glycyrrhizinate and mixtures thereof.

More particularly the terpenic acid derivative may be obtained from gum resin of *Boswellia serrata*.

In embodiments, the skin engaging member may comprise from 0.001 to about 10% of the thermally tolerant skin active ingredient capable of treating and/or preventing skin redness or skin irritation, by weight relative to the total weight of the skin engaging member, specifically from about 0.1% to 8%, more specifically from about 0.5% to 6%.

In embodiments, the skin engaging member may comprise from 0.001 to about 10% of thermally tolerant skin active ingredient comprising at least one terpenic acid derivative, by weight relative to the total weight of the skin engaging member, specifically from about 0.1% to 8%, more specifically from about 3% to 6%, even more specifically about 5%.

In embodiments, the skin engaging member may comprise from 0.001 to about 10% of thermally tolerant skin active ingredient comprising strombine or salt of strombine, combined with a clay, by weight relative to the total weight of the skin engaging member, specifically from about 0.1% to 8%, more specifically from about 0.5% to 4%, even more specifically about 1%. For sake of clarity, it is mentioned that the ingredient is a mixture of strombine—or salt—and clay, as indicated.

Another aspect provides for a skin engaging member attached to a razor cartridge, the skin engaging member comprising at least one water-soluble material and a water-insoluble material wherein the skin engaging member comprises Dipotassium Glycyrrhizinate/Glycyrrhizate (DPG). In embodiments, the skin engaging member may comprise from 0.001 to about 10% of Dipotassium Glycyrrhizinate/Glycyrrhizate (DPG), by weight relative to the total weight of the skin engaging member, specifically from about 0.1% to 8%, more specifically about 1%.

A further aspect provides for a skin engaging member attached to a razor cartridge, the skin engaging member comprising at least one water-soluble material and a water-insoluble material wherein the skin engaging member comprises boswellic acid. In embodiments, the skin engaging member comprises from 0.001 to about 10% of boswellic acid, by weight relative to the total weight of the skin engaging member, specifically from about 0.1% to 8%, more specifically about 5%.

In embodiments, a skin engaging member according to the present disclosure may comprise, in % by weight, from 10% to 100% of water-insoluble material by weight relative to the total weight of the skin engaging member, from 0.001% to 90% of water-soluble material by weight relative to the total weight of the skin engaging member, and/or 0.001% to 15% of other ingredients by weight relative to the total weight of the skin engaging member.

The other ingredients may be selected from the group comprising plasticizers in particular low molecular weight polyethylene glycols; water-swellable release enhancing agents in particular cross-linked polyacrylics and/or maleic anhydride compounds; additional lubricants; compatibilizers; surfactants; colorants; and/or skin care agents selected in the group consisting of vitamins, botanical extracts, salts, humectants, fragrances, essential oils, silicon oils, organic oils, waxes, antioxidants, exfoliants, depilatory agents, surfactants, hair and skin conditioning agents, anti-bacterial agents, anti-microbial, anti-irritants, antiseptics, biocides, preservatives, skin cooling and soothing agents, moisturizing and hydrating agents, skin protectants, colorants, film formers, processing thickening agents from the list of silica, fumed silica, $TiO_2$ particles, astringents, medicinal agents, soap base, emollient, beard softeners and mixtures thereof.

The other ingredients that are skin protectant, anti-irritant, anti-redness, are different from the terpenic acid derivative, also different from the combination of strombine—or salt of strombine—and with clay according to the disclosure.

The at least one water-soluble material, e.g. a lubricating polymer, may be dispersed in the water-insoluble material forming an immiscible blend.

It can be understood that "water-insoluble material" means a material that is insoluble in water at ordinary (room) temperature (25° C.) and at atmospheric pressure (1 atm/760 mmHg), and more specifically it has a solubility of less than 5% and particularly of less than 1% and more particularly of less than 0.1%. An indicative example of water-insoluble material that is known is high impact polystyrene (HIPS) that can be mixed with water-soluble materials, such as polyethylene glycols (PEGs) resulting in a blend where the water-insoluble material remains insoluble in contact with water while being mixed with water-soluble materials in any ratios. As "water-soluble" materials, it can be understood compounds such as polyethylene glycols or polyethylene oxides, wherein their chemical nature allows completely dissolution in presence of water, working thus as lubricating compounds.

In embodiments, the skin engaging member may comprise a thermally tolerant skin active ingredient capable of treating and/or preventing skin redness or skin irritation, wherein this skin active ingredient is strombine, a salt of strombine, or mixtures thereof in combination with a clay.

In embodiments, the skin active ingredient being strombine, a salt of strombine, or mixtures thereof, comprises a clay selected from the group comprising kaolinite, montmorillonite-smectite, illite, chlorite, bentonite, and any other suitable carrier/inert vector, particularly bentonite, or mixtures thereof.

Indeed, strombine or its salt, particularly silver salt, is a skin active ingredient that contributes to the cosmetic effect or treating or preventing skin irritation or skin redness. Moreover, strombine is a hydrophilic ingredient with two hydroxy groups to have more affinity with the water-soluble material.

The clay, particularly bentonite, acts on the one hand as carrier/inert vector, and on the other hand as a strombine or strombine salt protector. Indeed, the clay safeguards that the strombine, or strombine salt, sustains the high temperatures and high pressures observed during the shaving aid production, particularly extrusion, injection, injection-molding for example. The clay protects the strombine and contributes the thermal resilience. This is allowed e.g. by the clay melting point temperature; for example, bentonite has a melting point that reaches 1000° C.; the clay can thus increase the active substance's heat resistance.

The salt of strombine may be selected from the group comprising sodium, disodium, ammonium, lithium, magnesium, calcium, manganese, silver, and alkali metal salts. In some advantageous embodiments, it is a silver salt of strombine, i.e. silver carboxymethylalaninate.

In embodiments, the strombine salt can be silver carboxymethylalaninate.

The skin active ingredient may be a mixture comprising bentonite and silver salt of strombine marketed under the tradename INACALM® by Inabata Inc, Sumitomo Group, Japan.

Strombine is the active substance of the skin active ingredient and may be L-Strombine or D-Strombine. In embodiments, it may specifically be in the form of L-strombine.

Strombine and its salts, as well as method for producing it are described in detail in WO2016016582. The compositions described in WO2016016582 are cosmetic formulations that are produced according to traditional cosmetic process using soft conditions of temperature, pressure and/or shear. The said compositions manufacturing do not encounter conditions of temperature such that the one used in the extrusion of a shaving aid or skin engaging member of razor cartridge. Therefore, the problem of stability of strombine in the conditions of WO2016016582 never occurred.

It is the present disclosure that, for the first time, uses a skin active ingredient containing strombine in a skin engaging member attached to a razor cartridge, wherein the strombine or its salt, particularly silver salt, of the skin active ingredient is protected from heat alteration and degradation thanks to its association with a protector, such as a clay, particularly bentonite.

The skin active ingredient comprising strombine or a salt thereof may be the commercial product known as INACALM®, which is composed of bentonite, strombine and silver oxide. This product is manufactured and sold by Inabata Inc, Sumitomo Group, Japan.

While known for inclusion in cosmetic compositions such as cream or serums, it is for the first time that a combination of strombine or its salt with a clay is disclosed and used in a skin engaging member for razor, where manufacturing process involves high temperatures and/or high shear forces. The protective effect of the clay is indeed reported here for the first time. This allows to preserve and keep the properties of strombine in the skin engaging member, thus avoiding to deliver it by application of a cream or lotion prior or after shaving. The convenience of the user is thus improved.

The thermally tolerant skin active ingredient capable of treating and/or preventing skin redness or skin irritation comprising strombine or a salt thereof, contains in particular silver salt of strombine, in about 0.5% by total weight of the skin active ingredient.

In particular, the thermally tolerant skin active ingredient capable of treating and/or preventing skin redness or skin irritation comprising strombine or a salt thereof, particularly silver salt of strombine, may comprise 0.5% of strombine in the form of silver salt, 99.5% of clay, e.g. bentonite, by total weight of the skin active ingredient.

The commercial product name as INACALM® contains biomimetic active ingredient, with soothing and calming properties, which significantly improves skin imperfections: redness and damage caused by bacterial outbreaks.

In some embodiments, the skin engaging member may comprise a thermally tolerant skin active ingredient capable of treating and/or preventing skin redness or skin irritation wherein the skin active ingredient is a terpenic acid derivative.

Triterpenes and terpenic acids derivatives are widely distributed in plants, and in many cases are the principles responsible for their anti-inflammatory effects. Some triterpenes are active against inflammatory enzymes like 5-lipoxygenase, elastase and phospholipase $A_2$. Others inhibit histamine, collagenase and interleukin release, lipid peroxidation and free radical-mediated processes, metabolism of endogenous corticoids, and complement and protein-kinase activities. It has been found that thermally tolerant terpenic acid derivatives can be introduced in a shaving strip, such as a skin engaging member, typically manufactured according to technologies involving high temperature and/or high shear such as extrusion or injection-molding substantially as explained herein.

It has been found that the retention—in quantity and/or in quality—of the skin active ingredient in the skin engaging member is achieved due to the low volatility of the terpenic acid derivatives and or by the protective role of the clay that may be combined with the skin active ingredient when this latter is strombine or salt thereof.

Without being bound by theory, such a behaviour can thus be explained by the high molecular weight of the terpenic acid derivatives compounds in combination with the chemical groups of those that can establish hydrogen bonds with the water-soluble material of the matrix of the skin engaging member. On the other hand, in respect of strombine and its salt, the clay having a very high fusion temperature, it is believed that it acts as a heat shield vis à vis strombine or strombine salt. Indeed, for conventional skin engaging member manufacturing processes, extrusion or injection molding for example, one encounters range of temperature process from about 150 to about 300° C., process pressure conditions between 250-2000 bar and process duration from 2 to 15 minutes.

In embodiments, the terpenic acid derivative or its salts may be triterpenic compounds or tetraterpenic compounds or polyterpenic compounds, specifically having at least 30 carbon atoms. More specifically, triterpenic or tetraterpenic compounds may contain from 30 to 50 carbon atoms. In particular, the "terpenic acid derivative" may be a pentacyclic triterpenoid compound. It will be understood that "pentacyclic" means that the compound comprises five rings. A triterpenoid may be understood in the broadest sense as a compound that is structurally derivable from a triterpene, i.e., a terpene obtainable from six isoprene units. The pentacyclic triterpenoid compound can also be interchangeably used with the term pentacyclic triterpenic compound. The pentacyclic triterpenoid compounds also comprise salts, such as the salts obtained from the terpenoid acids in combination with potassium or ammonium, specifically dipotassium.

In embodiments, the terpenic acid derivative can be understood as pentacyclic triterpenoid compound comprising at least one (unbound) hydroxyl group (—OH), or at least one acetylated hydroxyl group (—O+—CO—CH3) and/or at least one carbonyl group (C=O) at the A ring of the pentacyclic triterpenoid compound, i.e. a pentacyclic triterpenoid compound bearing a —OH, —O—CO—CH3 or an =O group attached to the C-atom in position 3. In embodiments, the terpenic acid derivative can be understood as pentacyclic triterpenoid compound that are covalently conjugated with one or more sugar moieties, such as glycyrrhetinic acid/glycyrrhizic acid. Particularly, the sugar moiety is conjugated with the pentacyclic triterpenoid compound at the C-atom of position 3.

The pentacyclic triterpenoid compound may also be described by the following structure according to formula (I):

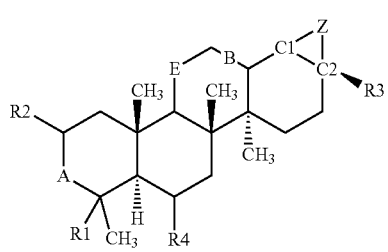

wherein:
R1 is selected from the group consisting of —CH$_3$, —CH$_2$OH,
and —COO—X$^+$, wherein X$^+$ is a proton or a cosmetically
acceptable cation;
R2 is hydrogen or —OH;
R3 is selected from the group consisting of —COO—X$^+$, —CH$_3$, and —COORa, wherein X$^+$ is a proton or a cosmetically acceptable cation and wherein Ra is a C$_{1-4}$-alkyl residue;
R4 is hydrogen or —OH;
C1 and C2 are each a carbon atom wherein the valency of C1 is replenished by hydrogen when the bond to z is a single bond;
z represents a bivalent residue selected from the groups consisting of

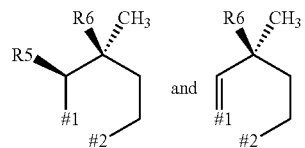

wherein:
1 represents the binding site to the carbon atom C1 of the remaining structure according to formula (I),
·2 represents the binding site to the carbon atom C2 of the remaining structure according to formula (I),
R5 is —CH$_3$ or hydrogen,
R6 is —CH$_3$, hydrogen, or —COO—X$^+$, and
A is a bivalent residue selected from the groups consisting of —CH(OH)—, —CH(OAc)—, —CO—, and —CH$_2$—; wherein "Ac" represents an acetyl moiety (—CO—CH$_3$)) or —CO—;
B represents a double or a single bond;
E represents —CH$_2$— or —CO—
In particular, wherein one of R1, R3 or R6 is —COO—X$^+$, wherein X$^+$ is a proton or a cosmetically acceptable cation.

Examples of triterpenic compounds as terpenic acid derivatives or its salts may include boswellic acid, such as alpha-boswellic acid, beta-boswellic acid, 3-O-Acetyl-β-boswellic acid, 11-Keto-β-boswellic acid, 3-O-Acetyl-11-Keto-β-boswellic acid, Acetyl-11-keto-β-boswellic acid, Acetyl-α-boswellic acid, 9,11-Dehydro-α-boswellic acid, 9,11-Dehydro-β-boswellic acid, Acetyl-9,11-dehydro-α-boswellic acid, Acetyl-9,11-dehydro-β-boswellic acid, glycyrrhetinic acid/glycyrrhizic acid and its salts, such as Ammonium Glycyrrhizate/Glycyrrhizinate, Diammonium Glycyrrhizate/Glycyrrhizinate, Potassium Glycyrrhizate/Glycyrrhizinate, Dipotassium Glycyrrhizate/Glycyrrhizinate, specifically Dipotassium Glycyrrhizate/Glycyrrhizinate and mixtures thereof.

Throughout the present description and claims, the expression "thermally stable" or "thermally tolerant" or "process tolerant" when used to describe the skin active ingredient capable of treating and/or preventing skin redness or skin irritation, e.g. anti-inflammatory skin active ingredient, refers to the ability of the ingredient to remain in quantitative concentration into the mixture of water-soluble and water-insoluble materials that form the skin engaging member wherein the concentration of the ingredient allows the ingredient to retain its biological activity (i.e. treating and/or preventing skin redness or skin irritation) following exposure to elevated temperatures ranging from 150 to 300° C., particularly from 150 to 250° C., and/or high shear forces and/or pressures, for a predetermined period of time.

Therefore and more particularly, throughout the present description and claims, the expression "thermally tolerant"

or "thermally stable" or "process tolerant" should thus be understood that the skin engaging member retains the contained skin active ingredient, after a thermal treatment/processing at about 150 to 300° C., from 2 to 15 minutes and pressure conditions between 250-2000 bar, in processes such as extrusion or injection or injection-molding, in concentration that is detected quantitatively at the end product/article, by applying analytical chemistry methods, such as liquid chromatography. In embodiments that the skin engaging member comprises skin active ingredient capable of treating and/or preventing skin redness or skin irritation and being selected from the group consisting of a) at least one terpenic acid derivative, b) strombine or salt of strombine, combined with a clay, and c) mixtures thereof, the concentration of the skin active ingredient retained after the thermal treatment/processing is about 0.001-100%, particularly 20-80%, more particularly 20-70%, of the initial quantity of skin active ingredient added. In embodiments that the skin engaging member comprises skin active ingredient being strombine or salt of strombine in combination with clay, the concentration of the skin active ingredient retained after the thermal treatment/processing is about 35-55% of the initial quantity of skin active ingredient added. In embodiments that the skin engaging member comprises skin active ingredient being boswellic acid, the concentration of the skin active ingredient retained after the thermal treatment/processing is about 35-70% of the initial quantity of skin active ingredient added. In embodiments that the skin engaging member comprises skin active ingredient being Dipotassium Glyccyrhizinate/Dipotassium Glycyrrhizate (DPG), the concentration of the skin active ingredient retained after the thermal treatment/processing is about 65-95% of the initial quantity of skin active ingredient added, even approximately 100% in some cases.

The quantity of the skin active ingredient in the skin engaging member can be measured/evaluated by (chromatographic) methods known to the skilled person depending on the nature of the active ingredient. Such methods can be found in monographs, guidelines, databases and information about analytical methods from the World Health Organization, scientific journals, literature, pharmacopoeias, producers and suppliers and the European Medicines Agency. The analytical extraction of such chemicals prior to analysis, can be performed with liquid-liquid extraction using organic solvents like ethanol, or even binary systems like hexane-water or other well-established extraction methods like solid phase extraction and others.

By utilizing any of the aforementioned methods, it is verified that the skin active ingredient retains its molecular structure, its molecular weight and its physicochemical properties and therefore it remains an active ingredient contributing skin care benefits. Further to the aforementioned methods, the process tolerance/thermal stability of the skin active ingredient is verified by comparing the analysis of skin active ingredient in the skin engaging member at the end of the production process with an analysis of equivalent skin active ingredients being pure (reference samples). Hence, the skin care effect of the skin active ingredient is also verified via clinical studies performed on the skin active ingredients when used in cosmetic applications. The clinical studies provide indication about the concentration ranges of skin active ingredients, within which the skin active ingredient contributes a cosmetic effect. By comparing the concentration of the skin active ingredient in the skin engaging member with the concentrations indicated as beneficial in the clinical studies, the skin care effect of the skin active ingredient is evaluated.

Each one of the aforementioned skin active ingredients can successfully be added in a blend of water-soluble material and water-insoluble material to construct a skin engaging member. Each one of the aforementioned skin active ingredients contributes individually a skin care property after sustaining the production process conditions. For any of the aforementioned skin active ingredients, the skin care effect is result of their presence in the final skin engaging member individually. This is further supported by the fact that each one the aforementioned skin active ingredient is process tolerant as evaluated individually. In other words, the skin engaging member is a simplified skin care system that sustains harsh production conditions and remains active to contribute skin care benefits. More specifically, such benefits can be achieved without combining the skin active ingredients with additional medicaments or other compounds with skin care properties, such as pyruvates and/or fatty acids as those known contributing to the repair of cellular membranes and resuscitation of mammalian cells. In addition, such benefits can be achieved without including the skin active ingredients in encapsulated form.

Example 1: Preparation of Skin Engaging Member Comprising Strombine or Salt of Strombine in Combination with Clay as Skin Active Ingredient Strombine in combination with clay is used as skin active ingredient in the skin engaging member. In a container, high impact polystyrene (HIPS) is added in concentration 23.45% and is blended with polyethylene glycol (PEG) being in concentration 75%. Butylated hydroxytoluene (BHT) as antioxidant is added in the blend in concentration 0.55%. The strombine in combination with clay is also added in the blend as skin active ingredient in initial concentration 1%. The blend in the container undergoes heating process till reaching melt temperature. The process conditions may include for example temperatures being within a range of 150° C. to 300° C. and pressure being between 250-2000 bar. In the meantime, the heated blend is processed via a rotating screw, from where the final skin engaging member is extruded in a desired shape according to the die head used in the extrusion system, such as in strip form. The reduction of the amount of strombine in combination with clay is 63% compared to the initial concentration, when measured in the final skin engaging member that is resulted from the process described.

Example 2: Preparation of Skin Engaging Member Comprising Boswellic Acid as Skin Active Ingredient In a second example, boswellic acid is used as skin active ingredient in the skin engaging member following the process described in Example 1. The boswellic acid is added initially in concentration 1% in a mixture comprising high impact polystyrene (HIPS) in concentration 19.45% and polyethylene glycols (PEGs) in concentration 75%. Butylated hydroxytoluene (BHT) as antioxidant is also added in the blend in concentration 0.55%. The reduction of the amount of boswellic acid is 52.2% compared to the initial concentration, when measured in the final skin engaging member that is resulted from the process described in Example 1.

Example 3: Preparation of Skin Engaging Member Comprising Dipotassium Glyccyrhizinate/Dipotassium Glycyrrhizate (DPG) as Skin Active Ingredient In a third example, Dipotassium Glyccyrhizinate/Dipotassium Glycyrrhizate (DPG) is used as skin active ingredient in the skin engaging member following the process described in Example 1. The Dipotassium Glyccyrhizinate/Dipotassium Glycyrrhizate (DPG) is added initially in concentration 1% in a mixture comprising high impact polystyrene (HIPS) in concentration 23.45% and polyethylene glycols (PEGs) in concentration 75%. Butylated hydroxytoluene (BHT) as antioxidant is also added in the blend in concentration 0.55%. The reduction of the amount of Dipotassium Glyccyrhizinate/Dipotassium Glycyrrhizate (DPG) is 30% compared to the initial concentration, when measured in the final skin engaging member that is resulted from the process described in Example 1.

In embodiments, the terpenic acid derivative may be boswellic acid. Boswellic acid derivatives may comprise a series of pentacyclic triterpene molecules that are produced by plants in the genus *Boswellia*. Like many other terpenes, boswellic acids appear in the resin of the plant that exudes them; it has been found that boswellic acids make up about 30% of the resin of *Boswellia serrata*.

This non/low volatility that is supposed to be related with high molecular weight has been found to formulate a skin engaging member containing a terpenic acid derivative able to sustain high temperatures and/or high shear forces encountered during the manufacturing process of such shaving aid strips.

As said, in a particular embodiment the at least one terpenic acid derivative is a boswellic acid.

The boswellic acids belong to organic acids, consisting of a pentacyclic triterpene, a carboxyl group and at least one other functional group. Alpha-boswellic acid and beta-boswellic acid, $C_{30}H_{48}O_3$ both have an additional hydroxyl group; they differ only in their triterpene structure. Acetyl-alpha-boswellic acid and acetyl-beta-boswellic acid, $C_{32}H_{50}O_4$, replace the hydroxyl group with an acetyl group.

In embodiments, the terpenic acid derivative, particularly boswellic acid, may be obtained from gum resin of *Boswellia* plants.

Suitable extracts for use herein may be derived from the following *Boswellia* plants including *Boswellia Cartenii*, *Boswellia Frereana*, *Boswellia Bhau-dajaina*, *Boswellia Serrata* and *Boswellia Thurifera*. It has been found that particularly suitable extracts for used herein are derived from the *Boswellia Serrata*.

The extracts derived from *Boswellia* plants can comprise gums, oleo-gums, resins, essential oils and residues, or mixtures thereof. Specific extracts for use herein are gum resins.

The *Boswellia* gum resin extract useful herein comprises a mixture of active triterpenoid compounds more commonly known as boswellic acids. Boswellic acids have a pentacyclic structure based on 12-ursen-24-oic acid with differing substituents. Many individual boswellic acid compounds have been isolated from the *Boswellia* extract including [alpha]- and [beta]-boswellic acids and derivatives thereof. Of these, [beta]-boswellic acid and derivatives thereof are thought to be the active components.

A typical extract of a *Boswellia* plant suitable for use in the present disclosure may comprise a mixture of boswellic acids comprising at least one of 3a-hydroxyurs-12-ene-24-oic acid, 3a-acetoxyurs-12-ene-24-oic acid, 3a-hydroxyurs-12-ene-11-keto-24-oic acid and 3a-hydroxyurs-9,12-dien-24-oic acid and their mixtures.

*Boswellia* extracts suitable for use in embodiments of the present disclosure are commercially available for example from Sabinsa Corporation with the name BOSWELLIN®.

The thermally tolerant skin active ingredient capable of treating and/or preventing skin redness or skin irritation comprising gum resin of *Boswellia serrata* may thus be the commercial product known as BOSWELLIN®. This product is manufactured and sold by Sabinsa Corporation. The content of BOSWELLIN® is standardized to minimum 35% β-boswellic acids and minimum 70% organic acids.

The commercial product known BOSWELLIN® usually contains the gum resin of *Boswellia serrata*, with anti-inflammatory properties, attributed to the presence of boswellic acids. Thus, BOSWELLIN® contributes to trigger the anti-inflammatory process of the skin. Particularly, the gum resin of *Boswellia serrata* contains:

Monoterpenes (α thujene)
Diterpenes (macrocyclic diterpenoids such as incensole, incensole oxide)
Inoincencole oxide, a diterpene alcohol (serrtol)
Triterpenes (such as α- and β-amyrins)
Pentacyclic triterpenic acids (boswellic acids), where the four major pentacyclic triterpenic acids are B-Boswellic Acid (I), Acetyl-β-Boswellic Acid (II), 11-keto-β-Boswellic Acid (III), Acetyl-11-keto-β-Boswellic Acid (IV)
Tetracyclic triterpenic acids (tirucall-8,24-dien-21-oic acids)

In some embodiments, the skin engaging member may comprise a thermally tolerant skin active ingredient capable of treating and/or preventing skin redness or skin irritation being Dipotassium Glycyrrhizinate/Glycyrrhizate (DPG). Dipotassium Glycyrrhizinate/Glycyrrhizate (DPG) is a salt of glycyrrhizin, which can be isolated from the licorice root, and glycyrrhizinate/glycyrrhizate is a widely used anti-inflammatory agent.

Glycyrrhizin is metabolized to glycyrrhetinic acid. Glycyrrhizic acid, or its salt, is the main and sweet component of licorice.

Glycyrrhizic acid, or salt thereof, is extracted from the root of the licorice plant; *Glycyrrhiza glabra*. It is a triterpene heteroside with glycyrrhetinic acid (terpenic acid) part and a dimeric osidic part made of a dimer of glucuronic acid. Chemical name is: (3-beta, 20-beta)-20-carboxy-11-oxo-30-norolean-12-en-β-yl 2-O-beta-D-glucopyranuronosyl-alpha-D-glucopyranosiduronic.

Dipotassium Glycyrrhizinate/Glycyrrhizate (DPG) contains glycyrrhizin, which is the main active of the licorice and is 250 times as sweet as cane sugar, with soothing properties, which inhibits skin inflammation and helps in reducing stinging parameters, itching, pain, warm sensation.

It has been found that Glycyrrhizic acid, and particularly its salt, Dipotassium Glycyrrhizinate/Glycyrrhizate, is heat stable/tolerant. Again, without being bound to theory, one could explain this thermostability by the low volatility related with high molecular weight. Indeed, Glycyrrhizic acid and its salts are widely used in food applications that are intended to be baked and keeping the sweetness.

In chemistry and physics, volatility is usually quantified by the tendency of a substance to vaporize. Volatility is directly related to a substance's vapor pressure. At a given temperature, a substance with higher vapor pressure vaporizes more readily than a substance with a lower vapor pressure.

The skin engaging member according to embodiments of the disclosure provides a progressive release of the thermally tolerant skin active ingredient capable of treating and/or preventing skin redness or skin irritation from the mixture of water-soluble material and water-insoluble material. The water-soluble material continuously leaches out as lubricant during shaving to enhance shaving glideness and comfort. In embodiments, the water-insoluble material is a thermoplastic material.

Consequently, the skin engaging member contributes to the lubricating effect through continuously releasing lubricants (i.e. water-soluble material) and in parallel contributes to the skin care effect through releasing the thermally tolerant skin active ingredient capable of treating and/or preventing skin redness or skin irritation, that is co-released with the water-soluble material, wherein the active ingredient provides anti-redness, anti-irritation and more generally anti-inflammatory and soothing action.

Throughout the present description and claims, the term "skin engaging member" refers to a physical structure which engages skin for lubrication during shaving and may be of any type including, but not limited to, one or more fin elements, elongated filaments or protrusions, or nubs, or any other texture such as logos, designs, graphics. The skin engaging member may be upstanding or curved, flexible or rigid, may have planar or non-planar surfaces, may be contiguous, non-contiguous, patterned with any functional or decorative patterns of any shape and form, or any combination thereof.

The skin engaging member is usually made as a part of a razor blade cartridge including one or more razor blades supported in a housing made from polymer material.

The polymer material of the housing may be any suitable polymer as currently used to make razor blade cartridges such as acrylonitrile butadiene styrene (ABS), but also may be any vinyl polymers, nylons, carbonate polymers, aliphatic polymers or the like.

The attaching of the skin engaging member to the housing can be permanent and substantially immovable or movable. Alternatively, the attaching can be non-permanent, and the skin engaging member can be replaced for any reason such as customization and/or to extend lifetime of the razor, while the attaching can be conducted by different engineering methods like snap fit, co-injection, sliding coupling or other similar methods, for example.

The razor cartridge may comprise one or more blades and a skin engaging member in proximity to the blade(s). The skin engaging member is typically located at the rear portion of the cartridge but may also be located at the front portion of the cartridge, or it may be placed at both positions on the cartridge.

On the razor cartridge, the skin engaging member may be monolayer or multilayer, wherein the layers may be identical or different in the case of a multilayer skin engaging member.

The skin engaging member may be shaped in a continuous or discontinuous configuration.

The skin engaging member may be continuous over the entire surface of the cartridge.

The skin engaging member may be continuous over one portion of the surface of the cartridge.

In some embodiments, the skin engaging member may be in the form of a strip. In embodiments, the skin engaging member of the razor cartridge may be provided as a single strip or a plurality of strips of skin engaging member on the surface of the cartridge.

The skin engaging member may be in the form of a two or more strips that are intended to be in contact with the skin during shaving.

The skin engaging member may be positioned in the recess of the lubra strip, behind the blades, on the top surface of the cutting edges portion of blades or even in the guard bar, in front of blades of the cartridge. Alternatively, the skin engaging member may also be applied in any surface of the housing or it may be applied on auxiliary components of the razor, such as skin engaging surfaces extending around the housing (skin adaptor for example).

In embodiments, the water-insoluble material may comprise a rigid water-insoluble material, an elastic water-insoluble material or a combination thereof.

In embodiments, the water-insoluble material may comprise a rigid water-insoluble, an elastic water-insoluble material such as thermoplastic elastomer compounds (TPEs), specifically from thermoplastic poly-urethanes and/or silicone polymers, or a combination thereof.

In further embodiments, the water-insoluble material may comprise a rigid water-insoluble material, i.e. unelastic water-insoluble material that do not undergo deformation under reasonable amount of stress applied. The rigid water-insoluble material may be selected from the group comprising polystyrene, styrene co-polymers, polyethylene, polypropylene, polyacetal, acrylonitrile-butadiene-styrene copolymer, ethylene vinyl acetal copolymer, polylactic acid, polycarbonate, maleic anhydride ethylene co-polymer blends, polyether-containing block copolymers (e.g. with polyamide), or mixtures or copolymers thereof. In some embodiments, the water-insoluble material further comprises one or more additive.

In more embodiments, the water-insoluble material may comprise an elastic water-insoluble material, i.e. a 'rubber-like' water-insoluble material and/or a deformable water-insoluble material and/or a flexible water-insoluble material that return in its initial condition after a force applied on it. The elastic water-insoluble material may be selected from the group comprising thermoplastic elastomer compounds (TPEs), specifically from thermoplastic poly-urethanes and/or silicone polymers.

In embodiments, the water-soluble material may comprise a material selected from the group comprising polyethylene oxide, polyethylene glycol, polyvinyl pyrrolidone, polyacrylamide, polyhydromethymethacrylate, or mixture thereof or copolymers thereof. Specifically, water-soluble materials may be polymers, e.g. polyethylene oxides generally known as POLYOX (e.g. POLYOX WSR Coagulant commercially available by DOW Chemicals) and/or ALKOX (e.g. ALKOX E300 commercially available by Meisei).

In some embodiments, the water-soluble material may be a polyethylene oxide having a molecular weight comprised between 1 000 000 and 9 000 000 g/mol, specifically between 4 000 000 and 8 000 000 g/mol and more specifically between 5 000 000 and 7 000 000 g/mol, even more specifically between 100 000 and 500 000 g/mol, and even more specifically between 200 000 and 300 000 g/mol.

In some embodiments, the water-soluble material may be a polyethylene glycol, in particular a low molecular weight polyethylene glycol, such as a polyethylene glycol having a molecular weight comprised between 300 and 9 000 g/mol, specifically between 4 000 and 7 500 g/mol.

In embodiments, the skin engaging member may be a solvent-free composition.

Another aspect provides for a process for manufacturing a skin engaging member substantially as described herein, wherein the process comprises at least one of the steps of extruding, injection-molding, laminating or compression-molding a composition for being incorporated on a razor cartridge to form a skin engaging member, wherein the composition comprises at least a water-soluble material, a water-insoluble material and a thermally tolerant skin active ingredient capable of treating and/or preventing skin redness or skin irritation.

All of the components of the skin engaging member including the skin active ingredient may be blended prior to injection or extrusion.

Skin engaging members according to the present disclosure may be fabricated by any appropriate method, including, but not limited to, injection molding, pressing, impregnation, calendaring, rolling and extrusion, or combination thereof. Skin engaging member may particularly fabricated by injection molding and/or extrusion. All of the components of the skin engaging member are blended prior to injection molding or extrusion. In addition, color masterbatches may be included to enhance aesthetically the skin engaging member. For best results, the components are dried before processing.

The blended components form a lubricating compound that is shaped in pellet form. The pellets are loaded in a container for being extruded through a single or twin rotating screw extruder. The container is heated and the rotating screw assists the lubricating compound to accelerate toward a required melt temperature. The required melt temperature may be, for example, within a range of 150° C. to 300° C. and the pressures occurred in this process are between 250-2000 bar. The melted pellets may further be injection molded or extruded to obtain the form/design of the skin engaging member according to the shape of the mold used in the injection molding or the die head used in the extrusion system. The blended components for producing the skin engaging member may also undergo co-extrusion or co-injection processes to form the final skin engaging member.

Thus, the skin engaging member may be first manufactured and then attached on the razor cartridge.

In some embodiments, the skin engaging member may be co-injected with the razor cartridge.

Another aspect provides for a razor cartridge comprising a skin engaging member as described herein. The razor cartridge is of the type for use with a hair removal device such as razor tool or depilatory tool. The razor cartridge may be removable from or integral to the hair removal device.

The disclosure also relates to a hair removal device, characterized in that it is of the wet shave type comprising a blade member and a skin engaging member as described above, wherein the skin engaging member is adjacent to the blade member.

A further aspect provides for the use of a razor comprising a skin engaging member as described above for delivering a thermally tolerant skin active ingredient capable of treating and/or preventing skin redness or skin irritation as herein described, onto the skin during shaving.

The disclosure also relates to the use of a razor comprising a skin engaging member substantially as described herein for calming symptoms of irritated and dry and/or sensitive skin by delivering skin active ingredient onto the skin, wherein the skin active ingredient is a thermally tolerant skin active ingredient capable of treating and/or preventing skin redness or skin irritation and is progressively released from the skin engaging member during shaving, particularly wet shaving.

The razor may be used in particular for reducing unpleasant feelings faced such as stinging, burning, tightness, skin redness and for controlling, preventing or treating skin irritation/inflammation disorders during shaving.

The razor comprising a skin engaging member substantially as described herein is used for reducing skin imperfections, the skin imperfections being in particular redness, irritation and/or damages caused by bacterial outbreaks and/or inflammation disorders.

The disclosure is also directed to a skin engaging member as described herein for use in the prevention and/or the treatment of the symptoms of irritated and dry and/or sensitive skin and the redness and/or damages caused by bacterial outbreaks and/or inflammation disorders.

The present disclosure also relates to a shaving method comprising shaving with a razor comprising at least one skin engaging member as described above to deliver thermally tolerant skin active ingredient capable of treating and/or preventing skin redness or skin irritation onto the skin, wherein the skin active is progressively released from the skin engaging member during shaving, particularly wet shaving.

The disclosure also relates to a hair removal method with the delivering of a thermally tolerant skin active ingredient capable of treating and/or preventing skin redness or skin irritation as disclosed herein onto the skin comprising the steps of:

Providing a hair removal device comprising a skin engaging member as disclosed herein, and Applying the hair removal device on the skin, therefore at the same time contacting the skin with the skin engaging member to release the active ingredient on the skin surface.

Particularly, the hair removal method is a wet method and the applying step is achieved on wet skin.

As is evident from text presented above, a variety of embodiments are contemplated:

1. A skin engaging member attached to a razor cartridge, the skin engaging member comprising a water-insoluble material and a water-soluble material, wherein the skin engaging member comprises a thermally tolerant skin active ingredient capable of treating and/or preventing skin redness or skin irritation and being selected from the group consisting of:
at least one terpenic acid derivative or its salts,
strombine or salt of strombine, combined with a clay, and mixtures thereof.

2. The skin engaging member according to embodiment 1, wherein the salt of strombine is selected from the group comprising sodium, disodium, ammonium, lithium, magnesium, calcium, manganese, silver, and alkali metal salts, specifically silver.

3. The skin engaging member according to embodiment 1 or 2, wherein the clay is selected from the group comprising kaolinite, montmorillonite, smectite, illite, chlorite, bentonite and any other suitable carrier/inert vector, specifically bentonite or mixtures thereof.

4. The skin engaging member according to any of the preceding embodiments, wherein the at least one terpenic acid derivative or its salts is a triterpenic compound, specifically pentacyclic triterpenoid compound.

5. The skin engaging member according to any of the preceding embodiments, wherein the at least one terpenic acid derivative or its salt is selected from the group consisting of boswellic acid, such as alpha-boswellic acid, beta-boswellic acid, 3-O-Acetyl-β-boswellic acid, 11-Keto-β-boswellic acid, 3-O-Acetyl-11-Keto-β-boswellic acid, Acetyl-11-keto-β-boswellic acid, Acetyl-α-boswellic acid, 9,11-Dehydro-α-boswellic acid, 9,11-Dehydro-β-boswellic acid, Acetyl-9,11-dehydro-α-boswellic acid, Acetyl-9,11-dehydro-β-boswellic acid, Glycyrrhetinic acid/glycyrrhizic acid and its salts, such as Ammonium Glycyrrhizate/Glycyrrhizinate, Diammonium Glycyrrhizate/Glycyrrhizinate, Potassium Glycyrrhizate/Glycyrrhizinate, Dipotassium Glycyrrhizate/Glycyrrhizinate, specifically Dipotassium Glycyrrhizate/Glycyrrhizinate and mixtures thereof.
6. The skin engaging member according to any of preceding embodiments, wherein the at least one terpenic acid derivative or its salts is selected in the group consisting of boswellic acid, Dipotassium Glycyrrhizinate and mixtures thereof.
7. The skin engaging member according to any of embodiments 1 to 6, wherein the terpenic acid derivative is obtained from gum resin of *Boswellia serrata*.
8. The skin engaging member according to any of embodiments 1 to 7, wherein the skin engaging member comprises from 0.001 to about 10% of the thermally tolerant skin active ingredient, by weight relative to the total weight of the skin engaging member.
9. The skin engaging member according to any of embodiments 1 to 8, wherein the skin engaging member comprises from 10% to 100% of water-insoluble material by weight relative to the total weight of the skin engaging member, from 0.001% to 90% of water-soluble material by weight relative to the total weight of the skin engaging member, and/or from 0.001% to 15% of other ingredients by weight relative to the total weight of the skin engaging member.
10. The skin engaging member according to embodiment 9, wherein the other ingredients are selected in the group of plasticizers in particular low molecular weight polyethylene glycols; water-swellable release enhancing agents in particular cross-linked polyacrylics and/or maleic anhydride compounds; additional lubricants; compatibilizers; surfactants; colorants; and/or skin care agents selected in the group consisting of vitamins, botanical extracts, salts, humectants, fragrances, essential oils, silicon oils, organic oils, waxes, antioxidants, exfoliants, depilatory agents, surfactants, hair and skin conditioning agents, anti-bacterial agents, anti-microbial, anti-irritants, antiseptics, biocides, preservatives, skin cooling and soothing agents, moisturizing and hydrating agents, skin protectants, colorants, film formers, processing thickening agents from the list of silica, fumed silica, $TiO_2$ particles and mixtures thereof.
11. The skin engaging member according to any of the preceding embodiments, wherein the water-insoluble material comprises rigid water-insoluble material, elastic water-insoluble material, such as thermoplastic elastomer compounds (TPEs), specifically from thermoplastic poly-urethanes and/or silicone polymers, or a combination thereof.
12. The skin engaging member according to any of the preceding embodiments, wherein the water-insoluble material comprises a rigid water-insoluble material selected from the group comprising polystyrene, styrene co-polymers, polyethylene, polypropylene, polyacetal, acrylonitrile-butadiene-styrene copolymer, ethylene vinyl acetal copolymer, polylactic acid, polycarbonate, maleic anhydride ethylene co-polymer blends, polyether-containing block copolymers, or mixtures or copolymers thereof.
13. The skin engaging member according to any of the preceding embodiments, wherein the water-insoluble material further comprises one or more additive.
14. The skin engaging member according to any of the preceding embodiments, wherein the water-soluble material comprises a material selected from the group comprising polyethylene oxide, polyethylene glycol, polyvinyl pyrrolidone, polyacrylamide, polyhydromethymethacrylate, or mixture thereof or copolymers thereof.
15. The skin engaging member according to any of the preceding embodiments, wherein the skin engaging member is a solvent-free composition.
16. Use of a razor comprising a skin engaging member according to any of preceding embodiments, for wet or dry shaving, for prevention and/or treatment of symptoms of irritated skin, dry skin and/or sensitive skin by delivering thermally tolerant skin active ingredient capable of treating and/or preventing skin redness or skin irritation, onto the skin, wherein the active ingredient is progressively released from the skin engaging member during shaving.
17. Process for manufacturing a skin engaging member according to any of embodiments 1 to 13, wherein it comprises extruding, injection-molding, laminating or compression-molding a composition for being incorporated on a razor cartridge, wherein the composition comprises at least a water-soluble material, a water-insoluble material and a thermally tolerant skin active ingredient capable of treating and/or preventing skin redness or skin irritation.
18. Use of a razor comprising a skin engaging member according to any of preceding embodiments for calming symptoms of irritated and dry and/or sensitive skin by delivering skin active ingredient onto the skin, wherein the skin active ingredient is progressively released from the skin engaging member during shaving.
19. Use of a razor comprising a skin engaging member according to any of previous embodiments for reducing unpleasant feelings faced such as stinging, burning, tightness, redness and for controlling inflammation disorders during shaving.
20. Use of a razor comprising a skin engaging member according to any of previous embodiments for reducing skin imperfections, the skin imperfections being in particular redness and/or damages caused by bacterial outbreaks and/or inflammation disorders.
21. Process for manufacturing a skin engaging member according to any of previous embodiments, wherein it comprises extruding, injection-molding, laminating or compression-molding a composition for being incorporated on a razor cartridge, wherein the composition comprises at least a water-soluble material, a water-insoluble material and a thermally tolerant skin active ingredient capable of treating and/or preventing skin redness or skin irritation and being selected from the group consisting of:
at least one terpenic acid derivative or its salts,
strombine or salt of strombine, combined with a clay, and mixtures thereof.
22. Method of skin treatment for calming symptoms of irritated and dry and/or sensitive skin in a user in need thereof during shaving, comprising applying a razor comprising a skin engaging member according to any of previous embodiments.

The invention claimed is:
1. A process for manufacturing a skin engaging member, wherein the process comprises:
extruding, injection-molding, laminating, or compression-molding a composition at a processing temperature from 150° C. to 300° C. while at a pressure from 250 bar to 2000 bar into the skin engaging member; and incorporating the skin engaging member on a razor cartridge, wherein the composition comprises at least a water-soluble material, a water-insoluble material, and a skin active ingredient that is thermally tolerant and capable of treating and/or preventing skin redness or skin irritation, wherein the skin active ingredient is selected from the group consisting of strombine combined with a clay, and a salt of strombine combined with a clay.

2. The process according to claim 1, wherein the salt of strombine is selected from the group consisting of: sodium, disodium, ammonium, lithium, magnesium, calcium, manganese, silver, and alkali metal salts.

3. The process according to claim 1, wherein the clay is selected from the group consisting of: kaolinite, montmorillonite, smectite, illite, chlorite, bentonite, any other suitable carrier/inert vector, and any mixtures thereof.

4. The process according to claim 1, wherein the skin engaging member comprises from 0.001 to about 10% of the skin active ingredient, by weight relative to a total weight of the skin engaging member.

5. The process according to claim 1, wherein the skin engaging member comprises from 10% to 100% of water-insoluble material by weight relative to a total weight of the skin engaging member, from 0.001% to 90% of water-soluble material by weight relative to the total weight of the skin engaging member, and/or from 0.001% to 15% of other ingredients by weight relative to the total weight of the skin engaging member.

6. The process according to claim 1, wherein the water-insoluble material comprises rigid water-insoluble material or elastic water-insoluble material, or a combination thereof.

7. The process according to claim 1, wherein the water-insoluble material comprises a rigid water-insoluble material selected from the group consisting of: polystyrene, styrene co-polymers, polyethylene, polypropylene, polyacetal, acrylonitrile-butadiene-styrene copolymer, ethylene vinyl acetal copolymer, polylactic acid, polycarbonate, maleic anhydride ethylene co-polymer blends, polyether-containing block copolymers, and any mixtures and any copolymers thereof.

8. The process according to claim 1, wherein the water-soluble material comprises a material selected from the group consisting of: polyethylene oxide, polyethylene glycol, polyvinyl pyrrolidone, polyacrylamide, polyhydromethymethacrylate, and any mixtures thereof, and any copolymers thereof.

9. The process according to claim 1, further comprising:
blending, prior to the extruding, injection-molding, laminating, or compression-molding, the water-soluble material, the water-insoluble material, and the skin active ingredient into a blended composition.

10. The process according to claim 9, further comprising:
drying, after the blending, the blended composition into pellets; and
melting the pellets prior to the extruding, injection-molding, laminating, or compression-molding.

11. The process according to claim 9, wherein the composition is co-injected with the razor cartridge.

12. The process according to claim 1, wherein the skin active ingredient is a salt of strombine combined with a clay, and wherein the skin engaging member comprises 0.5% to 4% of the skin active ingredient by weight relative to the total weight of the skin engaging member.

13. The process according to claim 1, wherein the water-soluble material is a lubricating polymer, and wherein the process further comprises: dispersing the lubricating polymer in the water-insoluble material to form an immiscible blend.

14. The process according to claim 13, wherein the lubricating polymer is polyethylene glycol (PEG) or polyethylene oxide and the water-insoluble material is high impact polystyrene (HIPS).

* * * * *